US00PP25071P2

(12) United States Plant Patent
Mansfield

(10) Patent No.: US PP25,071 P2
(45) Date of Patent: Nov. 18, 2014

(54) ***PANDOREA* PLANT NAMED 'PWS01'**

(50) Latin Name: ***Pandorea pandorana* ssp. *pandorana***
Varietal Denomination: PWS01

(71) Applicant: Daniel Mansfield, Skye (AU)

(72) Inventor: Daniel Mansfield, Skye (AU)

( * ) Notice: Subject to any disclaimer, the term of this patent is extended or adjusted under 35 U.S.C. 154(b) by 0 days.

(21) Appl. No.: 13/573,523

(22) Filed: Sep. 20, 2012

Related U.S. Application Data

(60) Provisional application No. 61/626,124, filed on Sep. 21, 2011.

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Annette Para
(74) *Attorney, Agent, or Firm* — Penny J. Aguirre

(57) ABSTRACT

A new cultivar of *Pandorea*, 'PWS01', that is characterized by its flowers that orange in color with creamy white on the inner surface of the lobes and suffused with purple-red when they are newly opened, its lush green foliage with small leaves and short internodes, its well-branched stems, and its moderate growth habit.

2 Drawing Sheets

Botanical classification: *Pandorea pandorana* ssp. *pandorana.*

Variety denomination: 'PWS01'.

BACKGROUND OF THE INVENTION

The present invention relates to a new and distinct cultivar of *Pandorea pandorana* ssp. *Pandorana* and will be referred to hereafter by its cultivar name, 'PWS01'. 'PWS01' is a new cultivar of Wonga-wonga, a vine grown for use as an ornamental landscape plant.

'PWS01' resulted from on breeding program initiated by the Inventor in Skye, Australia in 1999 with the goal of developing new cultivars of *Pandorea* that are densely branched with medium vigor combined with unique flower colors.

'PWS01' resulted from a crosses made in August of 1999 between two unnamed plants of *Pandorea* as the parent parents that were selected for their flower color. Controlled cross-pollination occurred in both directions, the plants were protected from chance pollination, and 2,000 seedlings resulting from the crosses were grown out for evaluation. The male and female parents cannot be distinguished as the seeds were pooled. Plants that showed short internode lengths and smaller leaves were further selected and grown out for evaluation of their flower color. 'PWS01' was selected as a single unique plant in spring of 2004.

Asexual reproduction of the new cultivar was first accomplished by the Inventor using softwood stem cuttings in 2004 in Skye, Australia. The characteristics of this cultivar have been determined to be stable and are reproduced true to type in successive generations.

SUMMARY OF THE INVENTION

The following traits have been repeatedly observed and represent the characteristics of the new cultivar as grown outdoors in a trial plot for six years in Skye, Australia. These attributes in combination distinguish 'PWS01' as a unique cultivar of *Pandorea.*

1. 'PWS01' exhibits flowers that orange-yellow in color with creamy white on the inner surface of the lobes, the flowers are suffused with purple-red when they are newly opened.
2. 'PWS01' exhibits lush green foliage with small leaves and short internodes.
3. 'PWS01' exhibits well-branched stems.
4. 'PWS01' exhibits a moderate growth habit.

One of the parent plants of 'PWS01' differs from 'PWS01' in having flowers that are whiter in color and the other parent plant differs from 'PWS01' in having flowers that are redder in color, both parents also differed in having a less dense plant habit. 'PWS01' can be most closely compared to the cultivar 'Golden Shower' (not patented) which differs from 'PWS01' in having flowers that are golden-brown in color and a more vigorous growth habit. 'PWS01' can also be compared to the cultivars 'Snowbells' (not patented) and 'Ruby Belle' (not patented). 'Snowbells' differs from 'PWS01' in having white flowers and 'Ruby Belle' differs from 'PWS01' in having pink flowers.

BRIEF DESCRIPTION OF THE DRAWING

The accompanying colored photographs were taken in mid summer and illustrate the overall appearance and distinct characteristics of a 6 year-old plant the new *Pandorea* as grown in a trial garden in Skye, Australia.

The photograph in FIG. 1 provides an overall view of the growth habit of 'PWS01'.

Figure 1:
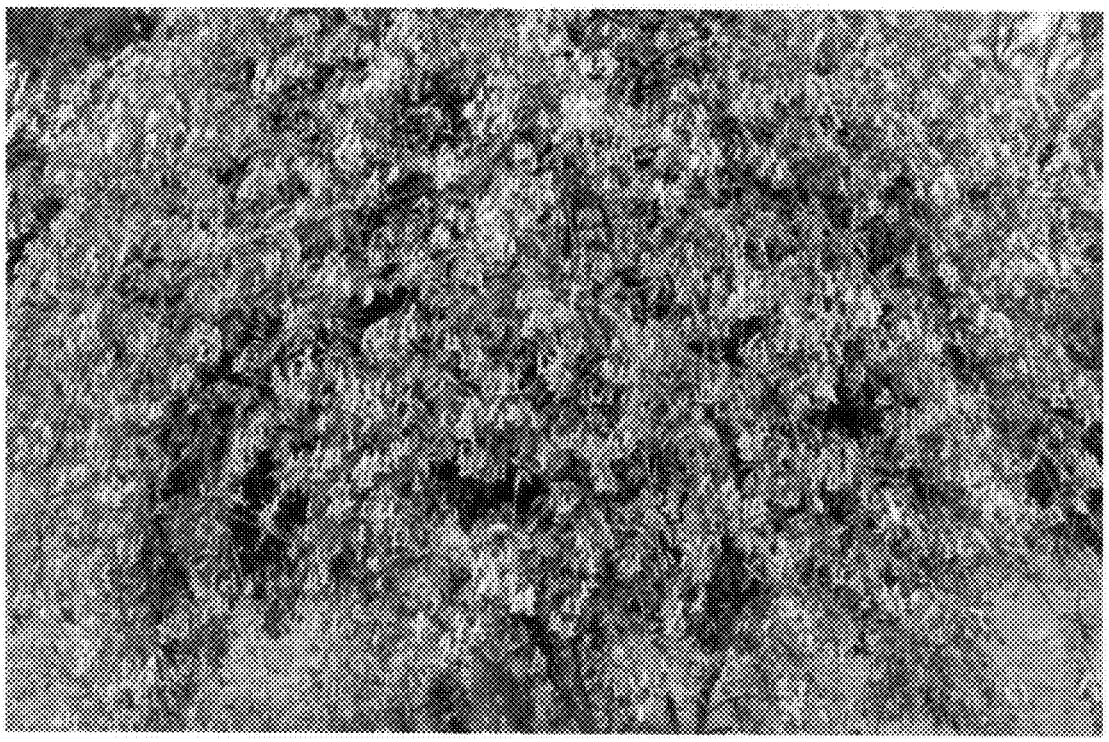
Figure 2:
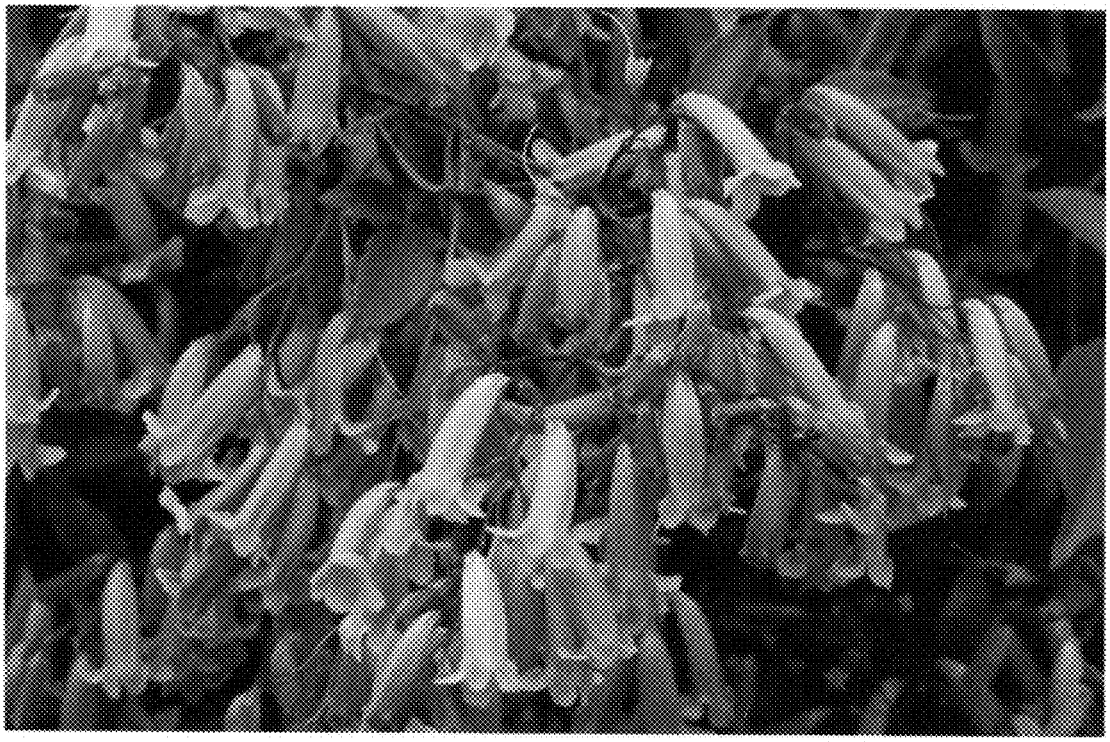

The photograph in FIG. 2 provides a close-up view of the inflorescences of 'PWS01'. The colors in the photographs may differ slightly from the color values cited in the detailed botanical description, which accurately describe the colors of the new *Pandorea.*

DETAILED BOTANICAL DESCRIPTION

The following is a detailed description of 1 year-old plants of the new cultivar as grown outdoors in a one-gallon container in Skye, Australia. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms from May through August in Skye, Australia.

*Plant habit*.—Dense, upright with arching vine-like lateral branches.

*Length*.—Reaches 60 cm in height and 30 cm in width in a one-gallon container.

*Hardiness*.—U.S.D.A. Zone 10.

*Diseases and pests*.—No susceptibility or resistance to diseases or pests has been observed.

*Root description*.—Fibrous.

Growth and propagation:

*Propagation*.—Softwood stem cuttings.

*Growth rate*.—Moderately vigorous.

Stem description:

*Shape*.—Oval.

*Stem color*.—New growth; 182B, mature wood; a blend of 199A and 199D.

*Stem size*.—Stem base; about 6 mm in diameter and 20 cm in length, lateral branches; an average of 2.5 mm in width and 40 cm in length, occasional secondary lateral branches an average of 6 cm in length and 2 mm in width.

*Stem surface*.—New growth; glabrous, mature wood finely barked.

*Branch internode length*.—Average of 6 cm.

*Branching*.—Average of 8 lateral branches per plant in a 1-gallon container.

Foliage description:

*Leaf shape*.—Ovate overall.

*Leaf division*.—Odd-pinnate with 3 to 5 leaflets.

*Leaf arrangement*.—Opposite.

*Leaf fragrance*.—None.

*Leaf internode length*.—An average of 4 cm.

*Leaflet shape*.—Primarily elliptic.

*Leaflet base*.—Cuneate.

*Leaflet apex*.—Acuminate.

*Leaflet venation*.—Pinnate, not conspicuous, color matches leaflet color on upper and lower surface.

*Leaflet margins*.—Entire and young leaves slightly crenate.

*Leaf attachment*.—Rachis is sessile to stem.

*Leaflet surface*.—Glabrous and satiny on upper surface and glabrous and dull on lower surface.

*Leaf size*.—Up to 11 cm in length and 7.5 cm in width, with leaflets an up to 4.5 cm in length and 2 cm in width.

*Leaf quantity*.—Average of 3 pair per branch 15 cm in length.

*Leaf color*.—Newly expanded leaves; upper and lower surface 145B, mature leaves; upper surface 137A, lower surface color 137C.

*Rachis*.—Average of 4.5 cm in length and 3 mm in width, 137C in color on upper surface and 144B in color on lower surface, sulcate in shape, glabrous surface, petiolules; none, sessile to rachis.

Inflorescence description:

*Inflorescence type*.—Terminal panicles of tubular flowers.

*Inflorescence size*.—Average of 2 cm in length and 1.4 cm in diameter.

*Flower buds*.—Oblong in shape, 59B in color with very apex 155B and sepal portion 59A an average of 1.8 cm in length and 6 mm in width.

*Flower fragrance*.—None detected.

*Lastingness of inflorescence*.—Inflorescence blooms for 4 weeks with individual flowers lasting about 3 to 5 days.

*Flower quantity*.—An average of 10 flowers per inflorescence, about 6 per plant grown in a 1-gallon container.

*Flower type*.—Tubular.

*Flower size*.—Average of 2 cm in diameter and 1.4 cm in depth.

*Peduncles*.—Average of 9 cm in length from apex to base of inflorescence and 2 mm in diameter, 182B in color, glabrous surface, oval in shape.

*Pedicels*.—Average of 1 cm in length and 0.7 mm in diameter, 182B in color, glabrous surface, oval in shape.

*Sepals*.—5, fused in campanulate form, 59A in color on upper and lower surface, un- fused portion in triangular shape; acute apex, about 1.5 mm in length and 2 mm in width on unfused portion, entire margin.

*Petals*.—5, fused into tube with apex of each free, fused portion is about 1.6 cm in length and 5 mm in width, free portion is about 4 mm in length and 4 mm in width, broadly acute-rounded apex and entire margin on lobes, outer surface is glabrous and inner surface has hairs about 1.5 mm in length and 8B in color, color of inner surface 158B and fading to 158C, color of outer surface 158B and strongly suffused with 59B fading to 158B and very slightly suffused with 59C.

Reproductive organs:

*Gynoecium*.—1 pistil, style is about 1.2 cm in length, and 151D in color, stigma is about 0.5 mm in diameter, globose in shape and 162C in color, ovary is oblong in shape, about 3 mm in length, 1 mm in diameter and 144B in color.

*Androcoecium*.—4 stamens, filaments are 155B in color, about 6 mm in length and curled inward, anthers (2 lobed) which each lobe about 2 mm in length and 182C in color on upper surface and 59B in color on lower surface, pollen could not be visualized.

*Fruit and seed*.—Not observed.

It is claimed:

1. A new and distinct cultivar of *Pandorea* plant named 'PWS01' as herein illustrated and described.

* * * * *